United States Patent
Cvetovich et al.

(12) 
(10) Patent No.: US 6,255,545 B1
(45) Date of Patent: Jul. 3, 2001

(54) PROCESS FOR THE SYNTHESIS OF 3,5-BIS (TRIFLUOROMETHYL)-BROMOBENZENE

(75) Inventors: Raymond Cvetovich, Scotch Plains; Fuh-Rong Tsay, Edison, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/590,853

(22) Filed: Jun. 8, 2000

Related U.S. Application Data

(60) Provisional application No. 60/138,883, filed on Jun. 11, 1999.

(51) Int. Cl.[7] .................................................. C07C 17/00
(52) U.S. Cl. ............................................ 570/191; 570/206
(58) Field of Search ...................................... 570/191, 206

(56) References Cited

U.S. PATENT DOCUMENTS 5,502,261   3/1996   Kleiner et al. .

FOREIGN PATENT DOCUMENTS

| 9-67297 | 3/1997 | (JP) . |
| 967297 | * 3/1997 | (JP) . |
| 9-169673 | 6/1997 | (JP) . |
| 9169673 | * 6/1997 | (JP) . |

OTHER PUBLICATIONS

Kunshenko, et al., *Zh. Org. Khim.*, 27 (1), 125–129 (1991) (English Translation).

Larionova, et al., *Zh. Prikl. Khim.* (*J. Applied Chemistry of the USSR*), 46 (9) 2012 (1973) (English Translation).

Porwisiak, et al., *Chem. Ber.*, 129 (2) 233–235 (1996).

* cited by examiner

*Primary Examiner*—Alan Siegel
(74) *Attorney, Agent, or Firm*—J. Eric Thies; David L. Rose

(57) ABSTRACT

The present invention is concerned with a novel process for the preparation of 3,5-bis(trifluoromethyl)bromobenzene (CAS 328-70-1). This compound is useful as an intermediate in the synthesis of compounds which possess pharmacological activity.

14 Claims, No Drawings

PROCESS FOR THE SYNTHESIS OF 3,5-BIS(TRIFLUOROMETHYL)-BROMOBENZENE

This application claims the benefit of the filing date of provisional patent application Ser. No. 60/138,883 filed Jun. 11, 1999.

BACKGROUND OF THE INVENTION

The present invention relates to processes for the preparation of 3,5-bis(trifluoromethyl)bromobenzene (CAS 328-70-1) which is useful as an intermediate in the preparation of certain therapeutic agents. In particular, the present invention provides a process for the preparation of 3,5-bis(trifluoromethyl)bromobenzene which is an intermediate in the synthesis of pharmaceutical compounds which are substance P (neurokinin-1) receptor antagonists.

The preparation of 3,5-bis(trifluoromethyl)bromobenzene by bromination of 1,3-bis(trifluoromethyl)benzene has been described various references. See for example: (a) Porwisiak, J; Schlosser, M. *Chem. Ber.,* 129(2), 233 (1996); (b) Kunshenko, B. V.; Omarov, V. O.; Muratov, N. N.; Mikhailevskii, S. M.; Yagupol'skii, L. M. *Zh. Org. Khim.,* 27(1), 125 (1991); (c) Larionova, Y. A.; Ponomarev, A. I.; Klebanskii, A. L.; Zaitsev, N. B.; Kol'tsov, A. I.; Motsarev, G. V.; Rozenberg, V. R. *Zh. Prikl. Khim.,* 46(9), 2012 (1973); (d) Furumata, T. (Central Glass Company, Ltd.) JP 9067297-A2 [J09067297] 97.03.11; Filing Date Aug. 28, 1995; (e) Suzuki, H. (Nissan Chemical Industries, Ltd., Japan) JP 9169673-A2 [J09169673] 97.06.30 Heisei; Filing Date Dec. 22, 1995. These references describe the preparation of 3,5-bis(trifluoromethyl)bromobenzene by brominating 1,3-bis(trifluoromethyl)benzene utilizing either N-bromosuccinimide (NBS) or 1,3-dibromo-5,5-dimethylhydantoin (DBH) in sulfuric acid or trifluoroacetic acid. The yields are quoted in the 90% range with isomeric and bis-brominated byproducts amounting to 5–10%. Efforts to repeat the procedures using methods with sulfuric acid as disclosed therein led to inconsistent yields of the desired product.

The general processes disclosed in the art for the preparation of 3,5-bis(trifluoromethyl)bromobenzene result in relatively low and inconsistent yields of the desired product. In contrast to the previously known processes, the present invention provides effective methodology for the preparation of 3,5-bis(trifluoromethyl)bromobenzene in relatively higher yield.

In accordance with the present invention, the use of acetic acid and/or a faster rate of stirring for the bromination of 1,3-bis(trifluoromethyl)benzene in sulfuric acid results in a more selective bromination of the starting material with higher yields of the product and lower amounts of bis-brominated byproducts.

It will be appreciated that 3,5-bis(trifluoromethyl)bromobenzene is an important intermediate for a particularly useful class of therapeutic agents. As such, there is a need for the development of a process for the preparation of 3,5-bis(trifluoromethyl)bromobenzene which is readily amenable to scale-up, uses cost-effective and readily available reagents and which is therefore capable of practical application to large scale manufacture.

Accordingly, the subject invention provides a process for the preparation of 3,5-bis(trifluoromethyl)bromobenzene via a very simple, short and highly efficient synthesis.

SUMMARY OF THE INVENTION

The novel process of this invention involves the synthesis of 3,5-bis(trifluoromethyl)bromobenzene. In particular, the present invention is concerned with novel processes for the preparation of a compound of the formula:

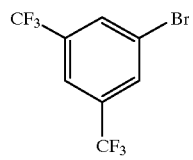

This compound is an intermediate in the synthesis of compounds which possess pharmacological activity. In particular, such compounds are substance P (neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of 3,5-bis(trifluoromethyl)bromobenzene of the formula:

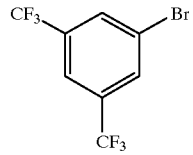

The general process for the preparation of 3,5-bis(trifluoromethyl)bromobenzene is as follows:

In a highly preferred embodiment, the present invention is directed to the preparation of 3,5-bis(trifluoromethyl)bromobenzene by the reaction of 1,3-bis-(trifluoromethyl)benzene with 1,3-dibromo-5,5-dimethylhydantoin in a mixture comprising glacial acetic acid and 96% sulfuric acid.

In accordance with the present invention, the use of acetic acid and/or a high rate of mixing in this reaction system increases solubilization of the starting material and results in less sensitivity to stirring parameters, as well as increased regioselectivity with respect to the position of bromination.

An embodiment of the present invention concerns a process for the preparation of 3,5-bis(trifluoromethyl)bromobenzene of the formula:

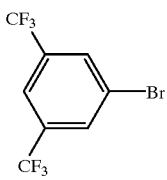

which comprises:
  treating a reaction mixture which comprises sulfuric acid, acetic acid, and 1,3-bis(trifluoromethyl)benzene of the formula:

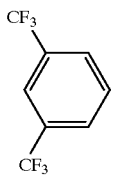

with a brominating agent to give 3,5-bis(trifluoromethyl)bromobenzene.

A preferred embodiment within the present invention concerns a process for the preparation of 3,5-bis(trifluoromethyl)bromobenzene of the formula:

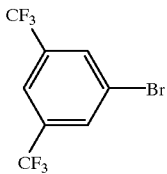

which comprises:
  treating a reaction mixture which comprises concentrated sulfuric acid, glacial acetic acid, and 1,3-bis(trifluoromethyl)benzene of the formula:

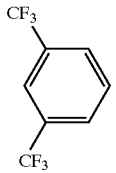

with a brominating agent selected from: N-bromosuccinimide and 1,3-dibromo-5,5-dimethylhydantoin, to give 3,5-bis(trifluoromethyl)bromobenzene.

Although numerous brominating agents may be employed in this process, N-bromosuccinimide (NBS) and 1,3-dibromo-5,5-dimethylhydantoin (DBH) are preferred, and 1,3-dibromo-5,5-dimethylhydantoin is more preferred.

This process is carried out in a solvent which comprises sulfuric acid and acetic acid, and which may additionally comprise water. The preferred solvent system is a mixture of sulfuric acid and acetic acid, and a more preferred solvent system is a mixture of concentrated sulfuric acid and glacial acetic acid. In the present invention it is preferred that the ratio of sulfuric acid:acetic acid is approximately 5:1 to 7:1 (v:v), and it is more preferred that the ratio of sulfuric acid:acetic acid is approximately 6:1 (v:v). In the present invention it is preferred that the sulfuric acid is added to the acetic acid at a controlled rate with cooling and rapidly mixing (such as with mechanical stirring).

In the present invention it is preferred that the ratio of the sulfuric acid/acetic acid to the 1,3-bis(trifluoromethyl)benzene substrate is approximately 2:1 to 1:2 (v:v). In the present invention it is more preferred that the ratio of the sulfuric acid/acetic acid to the 1,3-bis(trifluoromethyl)benzene substrate is approximately 1.5:1 (v:v). In the present invention it is preferred that the 1,3-bis(trifluoromethyl)benzene is added to the sulfuric acid:acetic acid at a controlled rate with cooling and rapidly mixing (such as with mechanical stirring).

In the present invention it is preferred that the reaction mixture is rapidly mixed (such as with mechanical stirring) and cooled upon treatment with the brominating agent. In the present invention it is preferred that the brominating agent is added to rapidly mixed reaction mixture which comprises sulfuric acid, acetic acid, and 1,3-bis(trifluoromethyl)benzene. In the present invention it is also preferred that the brominating agent is added to the reaction mixture in a controlled manner as individual portions.

The preferred temperature range following addition of the brominating agent is between about 10 and 70° C., a more prefered reaction temperature range is between about 40 and 50° C., and the most preferred temperature is about 45° C.

In a preferred embodiment, 1,3-bis(trifluoromethyl)benzene is brominated with N,N'-dibromo-5,5-dimethylhydantoin in sulfuric acid/acetic acid at 45° C. The reaction mixture is then diluted into cold water, and the phases are separated, washed with aqueous sodium hydroxide (preferably 5 N sodium hydroxide) and allowed to separate to produce 3,5-bis(trifluoromethyl)bromobenzene.

The product may contain approximately 2.6% isomeric impurities (which typically include 1,2-dibromo-3,5-bis(trifluoromethyl)benzene, 1,4-dibromo-3,5-bis(trifluoromethyl)bromobenzene, as well as small amounts of 2,4bis(trifluoromethyl)bromobenzene, 2,6-bis(trifluoromethyl)bromobenzene, and 3,5-bis(trifluoromethyl)biphenyl.

The 3,5-bis(trifluoromethyl)bromobenzene obtained in accordance with the present invention may be used directly without distillation as starting material in further reactions.

None of the references cited above discuss problems associated with low rates of mixing, nor do they mention brominations in a mixture of acetic acid and sulfuric acid. Surprisingly, in accordance with the present invention it was discovered that if the reaction is not stirred at an appropriate speed, the rate of bromination decreases, the yield of 3,5-bis(trifluoromethyl)bromobenzene drops, and production of isomeric, bis-brominated and tris-brominated byproducts increases to upwards of 30%. This indicates that more than one mechanism for the bromination reaction is operative in this system. Two reactions were performed on the same scale with N-bromosuccinimide (NBS) (1.05 eq) but at different stirrer speeds. The reactions were run in identical jacketed round bottom flasks, with identical stir bars and magnetic stirrers. The reaction rates differed as would be expected from a two-phase reaction, but the selectivity of the reactions were also different. The slower stirring reaction produced less product and more bis-brominated byproducts. Bromination of 1,3-bis(trifluoromethyl)benzene with N,N'-dibromo-5,5-dimethylhydantoin (DBH) is similarly facilitated by the use of acetic acid and/or a higher rate of mixing. Low stirring of the reaction mixture leads to slower, less selective brominations, and this effect is ameliorated by the use of acetic acid.

The effect of excess amounts of DBH on the bromination in sulfuric acid alone relative to the bromination in a combination of sulfuric acid/acetic acid was examined. Using a 5 mol % excess of DBH (10 mol % excess Br$^+$) at a slightly lower ratio of solvent: 1,3-bis(trifluoromethyl) benzene (3.2:1 v:v), the brominations were rapid. In sulfuric acid alone, however, bis-bromination of 3,5-bis (trifluoromethyl)bromobenzene continued after the starting material was completely consumed, whereas in sulfuric/acetic acid there was little or no loss to bis-bromination when 1,3-bis(trifluoromethyl)benzene was completely consumed. Accordingly, the use of sulfuric acid/acetic acid avoids consumption of the product 3,5-bis(trifluoromethyl) bromobenzene when excess brominating reagent is present.

Many of the starting materials are either commercially available or known in the literature and others can be prepared following literature methods described for analogous compounds. The skills required in carrying out the reaction and purification of the resulting reaction products are known to those in the art. Purification procedures include e.g., distillation, crystallization, normal phase or reverse phase chromatography.

The following examples are provided for the purpose of further illustration only and are not intended to be limitations on the disclosed invention.

EXAMPLE 1

3,5-Bis(trifluoromethyl)bromobenzene

| Materials | MW | Density | Amount | Mmol | Equiv. |
|---|---|---|---|---|---|
| 1,3-Bis(trifluoro-methyl)benzene | 214.1 | 1.38 | 107 g | 500 | 1.0 |
| 96% H$_2$SO$_4$ | | | 142 mL | | |
| Glacial HOAc | | | 22 mL | | |
| 1,3-Dibromo-5,5-dimethylhydantoin | 285.93 | | 77.25 g | 270 | 1.08 (Br$^+$) |
| 5N Aq NaOH | | | 75 mL | | |

To glacial acetic acid (22.0 mL), cooled to 15° C. in a 1 L 3-n RB flask (equipped with mechanical stirrer, thermocouple, and addition funnel), was added concentrated (96%) sulfuric acid (142 mL) in one portion. An exothermic heat of solution raised the temperature to 35° C. After cooling to 25° C., 1,3-bis(trifluoromethyl)benzene (107 g, 500 mmol) was added. With the acid mixture rapidly stirring, 1,3-dibromo-5,5-dimethylhydantoin (77.25 g; 270 mmol) was added over 2 min to give a multiple phase mixture (solid and two liquid). An exothermic reaction occured that raised the internal temperature to ~40° C. (jacket cooling at 15° C.). After the reaction temperature began to drop (after 5 min) the reaction mixture was maintained at 45° C. for 4.5 hr.

The rate and selectivity of the bromination is highly dependent on the agitation of the two phase reaction. Slower stirring increases the amount of bis-bromination and slows the overall rate of reaction. The reaction mixture remains heterogeneous throughout the reaction and the organic phase separates when agitation is interrupted. At the end of the reaction, the phases separate slowly (bromide density= 1.699). The rate of bromination is also dependent on the ratio of acetic to sulfuric acid.

Progress of the reaction is monitored by GC analysis, as follows. Sample: ~50 µl of mixed phase, dilute with cyclohexane (1.5 mL), wash with water (1 mL), then 2 N NaOH (1 mL), separate and inject. Resteck RTX-1701 [60 meter× 0.320 mm]: 100° C.; ramp: 5° C./min to 200° C.; 200° C. for 10 min; Flow 1.15 mL/min R$_t$:1,3-bis(trifluoromethyl)benzene: 7.0 min 3,5-bis(trifluoromethyl)bromobenzene: 9.4 min Biaryl: 19.2 min The mixture was cooled to 2° C. and poured slowly into cold water (250 mL). The mixture was stirred vigorously for 10 min, allowed to settle, and the lower organic layer was separated and washed with 5 N NaOH (75 mL) to give 145.1 g of a clear, colorless organic layer.

The assay yield of 1,3-bis(trifluoromethyl)bromobenzene was 93.7% (137.3 g, 469 mmol), which contained 0.6% 1,3-bis(trifluoromethyl)benzene, 1.0% 1,2-dibromo-3,5-bis (trifluoromethyl)benzene, and 0.3% 1,4-dibromo-3,5-bis-(trifluoromethyl)benzene. Total isomer byproducts measured by GC were 2.0 mol %.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

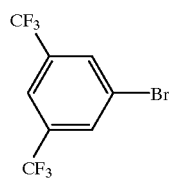

which comprises:

treating a reaction mixture which comprises sulfuric acid, acetic acid, and a compound of the formula:

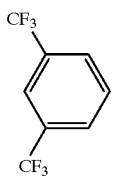

with a brominating agent selected from: N-bromosuccinimide and 1,3-dibromo-5,5-dimethylhydantoin, to give the compound of the formula:

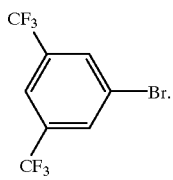

2. The process of claim 1 wherein the brominating agents is 1,3-dibromo-5,5-dimethylhydantoin.

3. The process of claim 1 wherein the reaction mixture comprises sulfuric acid and acetic acid.

4. The process of claim 1 wherein the reaction mixture comprises concentrated sulfuric acid and glacial acetic acid.

5. The process of claim 1 wherein the reaction mixture comprises sulfuric acid and acetic acid in which the ratio of sulfuric acid:acetic acid is approximately 5:1 to 7:1 (v:v).

6. The process of claim 5 wherein the reaction mixture comprises sulfuric acid and acetic acid in which the ratio of sulfuric acid:acetic acid is approximately 6:1 (v:v).

7. The process of claim 1 wherein the ratio of sulfuric acid/acetic acid to the substrate compound is approximately 2:1 to 1:2 (v:v).

8. The process of claim 7 wherein the ratio of sulfuric acid/acetic acid to the substrate compound is approximately 1.5:1 (v:v).

9. The process of claim 1 wherein the reaction mixture is rapidly mixed upon treatment with the brominating agent.

10. The process of claim 1 wherein the brominating agent is added to a rapidly mixed reaction mixture which comprises sulfuric acid, acetic acid, and 1,3-bis(trifluoromethyl) benzene.

11. The process of claim 1 wherein the temperature range following addition of the brominating agent is between about 10 and 70° C.

12. The process of claim 11 wherein the temperature range following addition of the brominating agent is between about 40 and 50° C.

13. The process of claim 12 wherein the temperature following addition of the brominating agent is about 45° C.

14. A process for the preparation of 3,5-bis(trifluoromethyl)bromobenzene which comprises contacting 1,3-dibromo-5,5-dimethylhydantoin with 1,3-bis(trifluoromethyl)benzene in a mixture comprising acetic acid and sulfuric acid to give 3,5-bis(trifluoromethyl)bromobenzene.

* * * * *